United States Patent [19]

Buchmann et al.

[11] Patent Number: 5,196,570

[45] Date of Patent: Mar. 23, 1993

[54] LEUKOTRIENE-B4 DERIVATIVES, PROCESS FOR THEIR PRODUCTION AND THEIR USE AS PHARMACEUTICAL AGENTS

[75] Inventors: Bernd Buchmann; Werner Skuballa; Joseph Heindl; Wolfgang Frohlich; Roland Ekerdt, all of Berlin, Fed. Rep. of Germany

[73] Assignee: Schering Aktiengesellschaft, Berlin and Bergkamen, both of Fed. Rep. of Germany

[21] Appl. No.: 602,283

[22] PCT Filed: Mar. 16, 1990

[86] PCT No.: PCT/DE90/00211

§ 371 Date: Nov. 16, 1990

§ 102(e) Date: Nov. 16, 1990

[87] PCT Pub. No.: WO90/11271

PCT Pub. Date: Oct. 4, 1990

[30] Foreign Application Priority Data

Mar. 17, 1989 [DE] Fed. Rep. of Germany ....... 3909327

[51] Int. Cl.$^5$ .............................................. G07C 67/02
[52] U.S. Cl. ..................................... 560/254; 560/55; 562/465
[58] Field of Search .................. 560/254, 55; 562/465; 514/532

[56] References Cited

FOREIGN PATENT DOCUMENTS 0319900 6/1989 European Pat. Off. .

*Primary Examiner*—Paul J. Killos

*Attorney, Agent, or Firm*—Millen, White, Zelano and Branigan

[57] ABSTRACT

The invention relates to new leukotriene-B4 analogs of formula I,

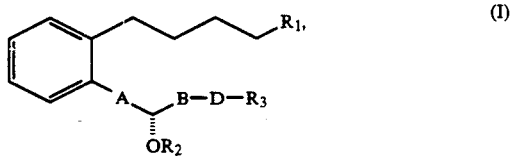

in which $R_1$ means radicals $CH_2OH$, $CH_3$, $CF_3$, $COOR_4$, or radical $CONHR_5$, A means a trans, trans—CH=CH—CH=CH— group, trans—CH$_2$—CH$_2$—CH=CH— group or tetramethylene group, B means a straight-chain or branched-chain, saturated or unsaturated alkylene group with up to 10 C atoms, D means a direct compound, oxygen, sulfur, a —C≡C—group or a —CH=CR$_6$—group, B and D together mean a direct bond, $R_2$ means a hydrogen atom or an acid radical of an organic acid with 1-15 C atoms and $R_3$ means a hydrogen atom, an optionally substituted alkyl radical with 1-10 C atoms, a cycloalkyl radical with 3-10 C atoms, an optionally substituted aryl radical with 6-10 C atoms or a 5-6-member heterocyclic radical and, if $R_4$ means a hydrogen atom, their salts with physiologically compatible bases and their cyclodextrin clathrates, process for their production and their pharmaceutical use.

15 Claims, No Drawings

LEUKOTRIENE-B₄ DERIVATIVES, PROCESS FOR THEIR PRODUCTION AND THEIR USE AS PHARMACEUTICAL AGENTS

The invention relates to new leukotriene-B$_4$ derivatives, the process for their production as well as their use as pharmaceutical agents.

Leukotriene-B$_4$ (LTB$_4$) was discovered in 1979 by B. Samuelsson et al. as a metabolite of arachidonic acid. In the biosynthesis, leukotriene A$_4$ is formed by the enzyme 5-lipoxygenase first as a central intermediate product, which then is converted by a specific hydrolase to the LTB$_4$.

inflammatory diseases, in which leukocytes invade the affected tissue.

It is known that LTB$_4$ causes the adhesion of leukocytes on the blood vessel wall. LTB$_4$ is chemotactically effective, i.e., it triggers a directed migration of leukocytes in the direction of a gradient of increasing concentration. Further, because of its chemotactic activity, it indirectly changes the vascular permeability, and a synergism with prostaglandin E$_2$ was observed. LTB$_4$ obviously plays a decisive role in inflammatory, allergic and immunological processes.

Leukotrienes and especially LTB$_4$ are involved in skin diseases, which accompany inflammatory processes (increased vessel permeability and formation of

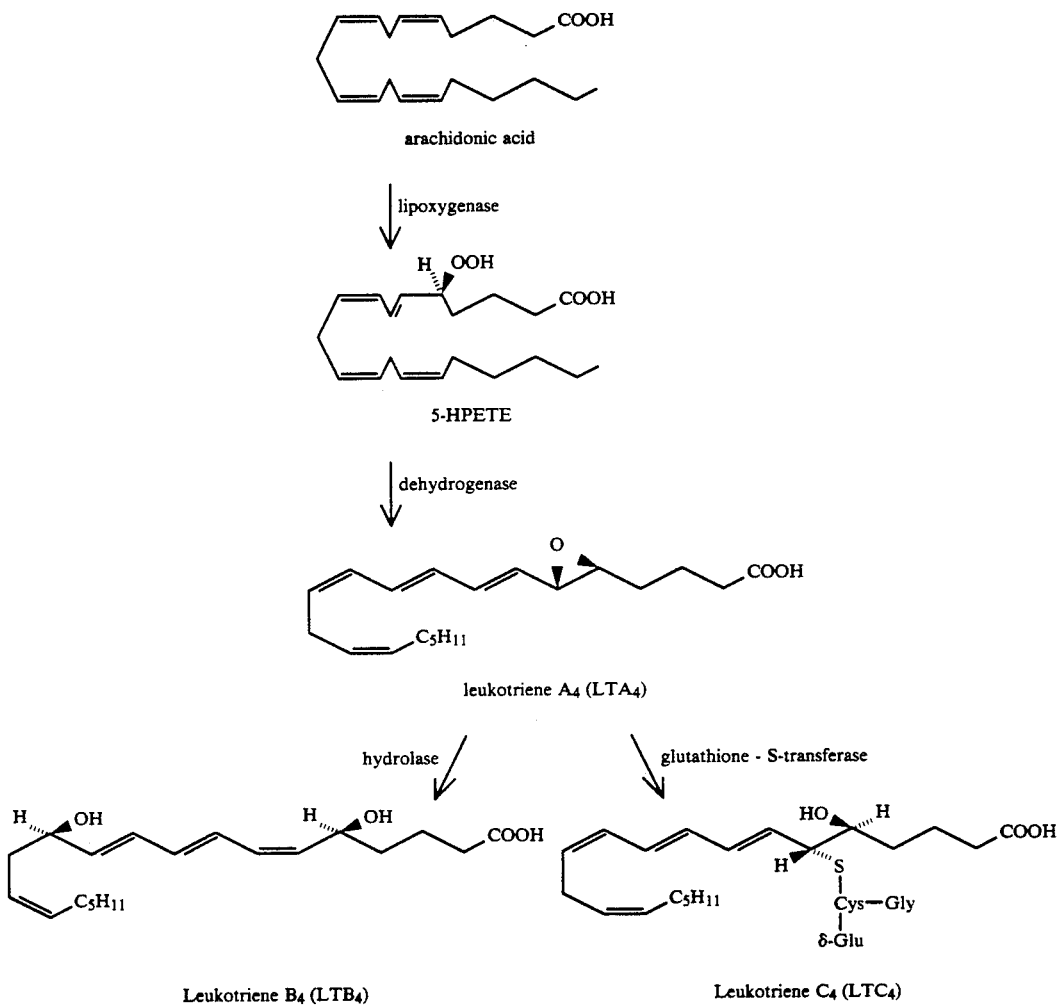

The nomenclature of the leukotrienes can be gathered from the following works:

a) B. Samuelsson et al., Prostaglandins 19, 645 (1980); 17, 785 (1979).

b) C. N. Serhan et al., Prostaglandins 34, 201 (1987).

The physiological and especially the pathophysiological importance of Leukotriene B$_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10 277 (1987). It follows from the above that LTB$_4$ is an important inflammation mediator for edemas, cell infiltration), increased proliferation of skin cells and itching, such as, for example, in eczemas, erythemas, psoriasis, pruritus and acne. Pathologically increased leukotriene concentrations are involved either casually in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and LTB$_4$ are involved especially in arthritis, chronic lung disease (e.g., asthma), rhinitis and inflammatory intestinal diseases.

Antagonists against LTB$_4$ itself or inhibitors of those enzymes, which are involved in the synthesis of the LTB$_4$, can be effective as specific medications, especially against diseases which accompany inflammations and allergic reactions.

Besides the therapeutic possibilities, which can be derived from an antagonizing of LTB$_4$ with LTB$_4$ analogs, the usefulness and potential use of leukotriene B$_4$ agonists for the treatment of fungus diseases of the skin was also able to be shown recently (H. Kayama, Prostaglandins 34, 797 (1988)).

The replacement of the chemically and metabolically liable cis-delta$^{6,7}$ double bond of LTB$_4$ by a 1,2-substituted phenyl ring results in the more stable 6,7-interphenylene-leukotrienes, and antagonists, agonists and partial antagonists are obtained depending on the structural change of the functional groups and depending on the tissue type. It has now been found that by the substitution of the 5-hydroxy group by a hydrogen atom and by other derivatizing of the functional groups, LTB$_4$ analogs are obtained which greatly antagonize the action of the natural LTB$_4$. Duration of action and selectivity of the new compounds could be further improved by lower oxidation sensitivity or the absence of a tendency toward lactonization because of the nonexistent 5-hydroxy group.

The invention relates to a new leukotriene-B$_4$ analogs of formula I,

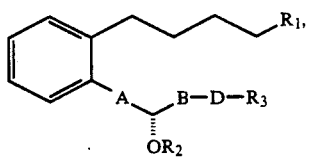

in which

R$_1$ means radical CH$_2$OH, CH$_3$, CF$_3$, or COOR$_4$ with R$_4$ meaning a hydrogen atom, an alkyl radical with 1-10 C atoms, a cycloalkyl radical with 3-10 C atoms, an aryl radical with 6-10 C atoms optionally substituted by 1-2 chlorine, bromine, phenyl, alkyl with 1-4 C atoms, chloromethyl, fluoromethyl, trifluoromethyl, carboxy, C$_1$-C$_4$ alkoxy or hydroxy, a —CH$_2$—CO aryl radical with 6-10 C atoms for an aryl or a 5-6-member heterocyclic radical with at least 1 heteroatom, radical CONHR$_5$ with R$_5$ meaning the radical R$_4$ or an alkanoyl radical or an alkanesulfonyl radical with 1-10 C atoms.

A means a trans, trans—CH=CH—CH=CH— group, trans—CH$_2$—CH$_2$—CH=CH— group or a tetramethylene group, B means a straight-chain or branched-chain, saturated or unsaturated alkylene group with up to 10 C atoms which can optionally be substituted by fluorine, or the group

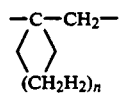

with n=1, 2 or 3,

D means a direct compound, oxygen, sulfur, a —C≡C— group or a —CH=CR$_6$ group with R$_6$ as hydrogen, C$_1$-C$_5$ alkyl, chlorine or bromine, B and D together mean a direct bond, R$_2$ means a hydrogen atom or an acid radical of an organic acid with 1-15 C atoms and R$_3$ means a hydrogen atom, an alkyl radical with 1-10 C atoms, an alkyl radical with 1-10 C atoms substituted by chlorine or bromine, a cycloalkyl radical with 3-10 C atoms, an aryl radical with 6-10 C atoms substituted optionally by 1-2 chlorine, bromine, phenyl, alkyl with 1-4 C atoms, chloromethyl, fluoromethyl, trifluoromethyl, carboxy, C$_1$-C$_4$ alkoxy or hydroxy or a 5-6-member heterocyclic radical with at least 1 heteroatom and, if R$_5$ means a hydrogen atom, their salts with physiologically compatible bases and their cyclodextrin clathrates.

As alkyl groups R$_4$ there are suitable straight-chain or branched-chain alkyl groups with 1-10 C atoms, such as, for example, methyl, ethyl, propyl, butyl, isobutyl, tert-butyl, pentyl, neopentyl, hexyl, heptyl, decyl. The alkyl groups R$_4$ can optionally be substituted one or more times by halogen atoms, alkoxy groups, optionally substituted aryl or aroyl groups, dialkylamino and trialkylammonium, in which case the simple substitution is to be preferred. As substituents, for example, there can be mentioned fluorine, chlorine or bromine, phenyl, dimethylamino, diethylamino, methoxy, ethoxy. As preferred alkyl groups R$_4$ those with 1-4 C atoms can be mentioned.

As aryl groups R$_4$ both substituted and unsubstituted aryl groups are suitable, such as, for example, phenyl, 1-naphthyl and 2-naphthyl which can each be substituted by 1-3 halogen atoms (F, Cl, Br), a phenyl group, 1-3 alkyl groups with 1-4 C atoms each, a chloromethyl, fluoromethyl, trifluoromethyl, carboxyl, hydroxy or alkoxy group with 1-4 C atoms. Preferred substituents in 3-and 4-position on the phenyl ring are, for example, fluorine, chlorine, alkoxy or trifluoromethyl, but in 4-position hydroxy or alkoxy groups.

The cycloalkyl groups R$_4$ can contain in the ring 3-10 carbon atoms preferably 5 and 6 carbon atoms. The rings can be substituted by alkyl groups with 1-4 carbon atoms. For example, there can be mentioned cyclopentylhexyl, cyclohexyl, methylcyclohexyl.

As heterocyclic groups R$_4$, 5- and 6-member heterocycles, which contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, i.a.

As acid radicals R$_5$ physiologically compatible acid radicals are suitable. Preferred acids are organic carboxylic acids and sulfonic acids with 1-10 carbon atoms, which belong to the aliphatic, cycloaliphatic, aromatic, aromatic-aliphatic and heterocyclic series. These acids can be saturated, unsaturated and/or polybasic and/or substituted in the usual way. As examples for the substituents, there can be mentioned alkyl groups, hydroxy groups, alkoxy groups, oxo groups or amino groups or halogen atoms. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, trimethylacetic acid, diethylacetic acid, tertbutylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid, benzoic acids substituted with halogen groups, trifluoromethyl groups, hydroxy groups, alkoxy groups or carboxy groups, nicotinic acid, isonicotinic acid, 2-furancarboxylic acid, cyclopentylpropionic acid. As especially preferred acyl radicals and alkanesulfonyl radicals, those with up to 6 carbon atoms are possible. As sulfonic acids, for example, methanesulfonic acid, ethanesulfonic acid, isopropanesulfonic acid, beta-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(betachloroethyl)aminosulfonic acid, N,N-diisobutylaminosulfonic acid, N,N-dibutylaminosulfonic acid, pyrrolidino-, piperidino-, piperazino-, N-methylpiperazino-and morpholinosulfonic acid are possible.

As alkyl groups $R_3$ straight- and branched-chain, saturated and unsaturated alkyl radicals, preferably saturated, with 1-10, especially 1-6 C atoms, are suitable, which optionally can be substituted by optionally substituted aryl. For example, there can be mentioned the methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups. If alkyl groups $R_3$ are halogen-substituted halogens fluorine, chlorine and bromine are suitable.

The cycloalkyl group $R_3$ can contain in the ring 3-10 carbon atoms, preferably 3-6 carbon atoms. The rings can be substituted by alkyl groups with 1-4 carbon atoms. For example, there can be mentioned cyclopropyl, cyclobutyl, cyclopentyl, cyclohexyl, methylcyclohexyl.

As substituted or unsubstituted aryl groups $R_3$ for example, phenyl, 1-naphthyl and 2-naphthyl, which can each be substituted by 1-3 halogen atoms, a phenyl group, 1-3 alkyl groups each with 1-4 C atoms, a chloromethyl group, fluoromethyl group, trifluoromethyl group, carboxyl group, $C_1-C_4$ alkoxy group or hydroxy group are suitable. The substitution in 3- and 4-position in a phenyl ring is preferable, for example, by fluorine, chlorine, alkoxy or trifluoromethyl or in 4-position by hydroxy or alkoxy groups.

As heterocyclic groups $R_3$ 5- and 6-member heterocycles that contain at least 1 heteroatom, preferably nitrogen, oxygen or sulfur, are suitable. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a.

As alkylene group B, straight-chain or branched-chain, saturated and unsaturated alkylene radicals with up to 10 C atoms, preferably saturated with 1-10, especially with 1-5 C atoms, which can be substituted optionally by fluorine atoms, are suitable. For example, there can be mentioned: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyl trimethylene, 1-methylene-ethylene, 1-methylene-tetramethylene.

As acid radicals $R_2$ physiologically compatible acid radicals are suitable. Preferred acids are organic carboxylic acids and sulfonic acids with 1-15 carbon atoms, which belong to the aliphatic, cycloaliphatic, aromatic, aromatic-aliphatic or heterocyclic series. These acids can be saturated, unsaturated and/or polybasic and/or substituted in the usual way. As examples for the substituents, there can be mentioned the alkyl, hydroxy, alkoxy, oxo or amino groups or halogen atoms.

For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid, benzoic acids substituted with halogen, trifluoromethyl, hydroxy, alkoxy or carboxy groups, nicotinic acid, isonicotinic acid, 2-furancarboxylic acid, cyclopentylpropionic acid. As especially preferred acid radicals $R_2$, acyl radicals with up to 10 carbon atoms are suitable.

Inorganic and organic bases are suitable for salt formation, as they are known to one skilled in the art for forming physiologically compatible salts. For example, there can be mentioned alkali hydroxides, such as sodium and potassium hydroxide, alkaline earth hydroxides, such as calcium hydroxide, ammonia, amines, such as ethanolamine, diethanolamine, triethanolamine, n-methylglucamine, morpholine, tris(hydroxymethyl)methylamine, etc.

The leukotriene-$B_4$ derivatives of formula 1 form the already mentioned cyclodextrin clathrates with alpha-, beta- gamma-cyclodextrin.

The invention further contains a process for the production of leukotriene-$B_4$ derivatives of formula I, which is characterized in that an aldehyde of formula II,

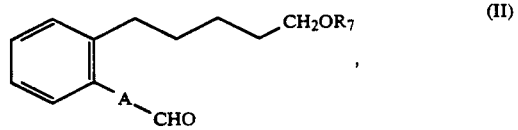

in which A has the above-indicated meaning and $R_7$ means an easily cleavable ether radical, such as, for example, dimethyl-tert-butylsilyl, trimethylsilyl, tribenzylsilyl, diphenyl-tert-butylsilyl, tetrahydropyranyl, tetrahydrofuranyl and alphaethoxyethyl, to mention only a few, is reacted with a magnesium organic compound of formula III,

in which X means chlorine, bromine or iodine and B, D and $R_3$ have the above-indicated meanings, and then is optionally separated into any sequence of enantiomers, protected hydroxy groups are released and/or a free hydroxy group is esterified and/or the 1-hydroxy group is oxidized to carboxylic acid and/or double bonds are hydrogenated and/or an esterified carboxyl group ($R_1$=COOR$_5$) is saponified and/or reduced and/or a carboxyl group ($R_5$=H) is esterified and/or a free carboxyl group ($R_5$=H) is converted to an amide ($R_1$=CONHR$_6$) or a carboxy group with a physiologically compatible base is converted to a salt.

The reaction of the compound of formula II with a organometallic compound of formula II takes place in a way known in the art in an inert solvent or solvent mixture, such as, for example, diethyl ether, tetrahydrofuran, dioxane, toluene, dimethoxyethane, preferably diethyl ether or tetrahydrofuran. The reaction is performed at temperatures between −100° C. and 60° C., preferably at −78° C. to 0° C.

The production of the compound of formula III needed for this reaction takes place by the reaction of the corresponding halide by reaction with magnesium.

The reduction to the compounds of formula I with $R_1$ meaning a —$CH_2OH$ group is performed with a reducing agent suitable for the reduction of esters or carboxylic acids, such as, for example, lithium aluminum hydride, diisobutyl aluminum hydride, etc. As solvents, diethyl ether, tetrahydrofuran, dimethoxyethane, toluene, etc., are suitable. The reduction is performed at temperatures of −30° C. up to the boiling temperature of the solvent used, preferably 0° C. to 30° C.

The esterification of the alcohols of formula I ($R_2$=H) takes place in a way known in the art. For example, the esterification takes place in that an acid derivative, preferably an acid halide or an acid anhydride, is reacted in the presence of a base such as, for example, Na hydride, pyridine, triethylamine, tributylamine or 4-dimethylaminopyridine with an alcohol of formula I. The reaction can be performed without a solvent or in an inert solvent, preferably acetone, acetonitrile, dimethylacetamide, DMSO at temperatures above or below room temperature, for example, between −80° C. to 100° C., preferably at room temperature.

The oxidation of the 1-hydroxy group is performed according to methods known to one skilled in the art. As oxidizing agents, for example, pyridinium dichromate (Tetrahedron Letters, 1979, 399), Jones reagent (J. Chem. Soc. 1953, 2555) or platinum/oxygen (Adv. in Carbohydrate Chem. 17, 169 (1962) or Collins oxidation and then Jones oxidation can be used. The oxidation with pyridinium chromate is performed at temperatures of 0° C. to 100° C., preferably 20° C. to 40° C. in a solvent, for example dimethylformamide, inert toward the oxidizing agent.

The oxidation with Jones reagent is performed at temperatures of −40° C. to 40° C., preferably 0° C. to 30° C. in acetone as a solvent.

The oxidation with platinum/oxygen is performed at temperatures of 0° C. to 60° C., preferably 20° C. to 40° C. in a solvent, such as, e.g., ethyl acetate, inert toward the oxidizing agent.

The saponification of the esters of formula I is performed according to methods known to one skilled in the art, such as, for example, with basic catalysts. The compounds of formula I can be separated by the usual separation methods into the optical isomers.

The release of the functionally modified hydroxy groups takes place according to known methods. For example, the cleavage of hydroxy protecting groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a suitably water-miscible inert organic solvent is added. Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protecting groups takes place, for example, with tetrabutylammonium fluoride or with potassium fluoride in the presence of a crown ether. As a solvent, for example, tetrahydrofuran, diethyl ether, dioxane, methylene chloride, etc. are suitable. The cleavage is performed preferably at temperatures between 0° C. and 80° C.

The saponification of the acyl groups takes place, for example, with alkali or alkaline-earth carbonates or hydroxides in an alcohol or in the aqueous solution of an alcohol. As an alcohol, aliphatic alcohols are suitable, such as, for example, methanol, ethanol, butanol, etc., preferably methanol. As alkali carbonates and alkali hydroxides, potassium and sodium salts can be mentioned. The potassium salts are preferred.

As alkaline-earth carbonates and hydroxides, for example, calcium carbonate, calcium hydroxide and barium carbonate are suitable. The reaction takes place at −10° C. to +70° C., preferably at +25° C.

The introduction of the ester group

for $R_1$, in which $R_4$ represents an alkyl group with 1–10 C atoms, takes place according to methods known to one skilled in the art. The 1-carboxy compounds are reacted, for example, with diazohydrocarbons in a way known in the art. The esterification with diazohydrocarbons takes place, i.e., in that a solution of the diazohydrocarbons in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389-394 (1954)].

The introduction of the ester group

for $R_1$, in which $R_4$ represents a substituted or unsubstituted aryl group, takes place according to methods known to one skilled in the art. For example, the 1-carboxy compounds with the corresponding arylhydroxy compounds in an inert solvent are reacted with dicyclohexylcarbodiimide in the presence of a suitable base, for example pyridine, DMAP, triethylamine. As a solvent, methylene chloride, ethylene chloride, chloroform, ethyl acetate, tetrahydrofuran, preferably chloroform are suitable. The reaction is performed at temperatures between −30° C. and +50° C., preferably at 10° C.

If C═C double bonds contained in the primary product are to be reduced, the hydrogenation takes place according to methods known in the art.

The hydrogenation of the delta$^{8,10}$-diene system is performed, in a way known in the art, at low temperatures, preferably at about −20° C. to +30° C. in a hydrogen atmosphere in the presence of a noble metal catalyst. As a catalyst, for example, 10% palladium on carbon is suitable.

The leukotriene-B4 derivatives of formula I with R4 meaning a hydrogen atom can be converted to a salt with suitable amounts of the corresponding inorganic bases with neutralization. For example, during dissolving of the corresponding acids in water, which contains the stoichiometric amount of the base, the solid inorganic salt is obtained after the evaporating off of the water or after the addition of a water-miscible solvent, e.g., alcohol or acetone.

For the production of an amino salt, the LTB4 acid, e.g., is dissolved in a suitable solvent, for example, ethanol, acetone, diethyl ether, acetonitrile or benzene, and at least the stoichiometric amount of the amine is added to this solution. In this way, the salt usually accumulates in solid form or is isolated after evaporation of the solvent in the usual way.

The introduction of the amide group

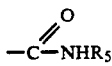

for R1 takes place according to methods known to one skilled in the art. The carboxylic acids of formula I (R4=H) are first converted in the presence of a tertiary amine, such as, for example, triethylamine, with chloroformic acid isobutyl ester to the mixed anhydride. The reaction of the mixed anhydride with the alkali salt of the corresponding amide or with ammonia (R5=H) takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

Another possibility for the introduction of the amide group

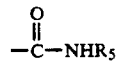

for R1 is in the reaction of a 1-carboxylic acid of formula I (R4=H), in which free hydroxy groups optionally are protected intermediately with compounds of formula IV

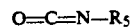    (IV)

in which R5 has the above-indicated meaning.

The reaction of the compound of formula I (R4=H) with an isocyanate of formula IV optionally takes place by adding a tertiary amine such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene at temperatures between −80° C. to 100° C., preferably at 0° C. to 30° C.

If the initial product contains OH groups in a leukotriene-B4 radical, these OH groups are also reacted. Finally, if end products are desired which contain the free hydroxyl groups, a start suitably is made from the initial products in which these are intermediately protected by preferably easily cleavable ether or acyl radicals.

The compounds of formula II used as initial material can be produced, for example, as follows:

The hydroxy group of 4-chlorobutanol in a way known in the art by reaction with a correspondingly substituted silyl chloride by base catalysts or, e.g., by reaction with a correspondingly substituted enol ether by acid catalysts is converted to the ether of formula V, and R7 has the above-indicated meaning

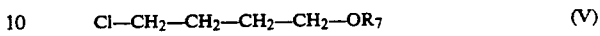    (V)

By alkylation of the dilithiated 2-methylbenzyl alcohol with the chloride of formula V, the alcohol of formula VI is obtained

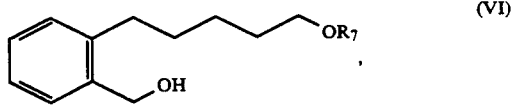    (VI)

which is converted by oxidation, e.g., with manganese dioxide to the aldehyde of formula VII

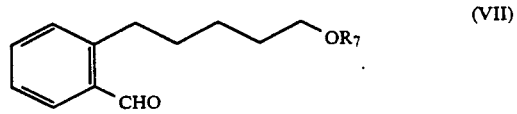    (VII)

By a Wittig-Horner olefinization of the aldehyde of formula VII with the phosphonate of formula VIII, subsequent reduction of the ester, for example, with DIBAH, hydrogenation of the double bond, oxidation of the alcohol with, e.g., Collins reagent to the aldehyde and another Wittig-Horner reaction with the phosphonate of formula VIII, or by Wittig-Horner olefinization of the aldehyde of formula VII with the phosphonate of formula IX and a base and optionally subsequent hydrogenation, the esters

    (VIII)

    (IX)

of formula X are obtained from the aldehyde of formula VII and A has the above-indicated meaning.

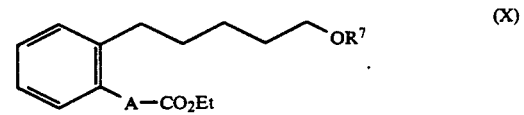    (X)

As bases for the above Wittig-Horner olefinization, for example, K-tert-butylate, diazobicyclononane or diazobicycloundecane or sodium hydride are suitable.

The reduction of the ester group, for example, with DIBAH and then oxidation of the primary alcohol obtained, e.g., with manganese dioxide or Collins reagent, results in the aldehyde of formula II.

The compounds of formula 1 act in an anti-inflammatory and anti-allergic manner. In addition, they have antimycotic properties. Consequently, the new leukotriene-B4 derivatives of formula 1 represent valuable pharmaceutical active ingredients. The compounds of formula I are especially suitable for topical application, since they exhibit a dissociation between desirable topical effectiveness and undesirable systemic side effects.

The new leukotriene-B$_4$ derivatives of formula 1 are suitable in combination with the auxiliary agents and vehicles usual in galenic pharmaceutics for topical treatment of contact dermatitis, eczemas of the most varied types, neurodermatosis, erythrodermia, burns, tinea, pruritus vulvae, pruritus ani, rosacea, lupus erythematosus cutaneus, psoriasis, lichen ruber planus and verrucosis and similar skin diseases.

The production of pharmaceutical agent specialties takes place in the usual way, by the active materials with suitable additions being converted into the desired form of application, such as, for example: solutions, lotions, ointments, creams or plasters. In the pharmaceutical agents thus formulated, the active ingredient concentration is dependent on the form of application. An active ingredient concentration of 0.0001% to 1% is used preferably in lotions and ointments.

Further, the new compounds optionally in combination with the usual vehicles and auxiliary agents are also very suitable for the production of inhalants, which can be used for the treatment of allergic diseases of the respiratory system such as, for example, bronchial asthma or rhinitis.

Further, the new leukotriene-B$_4$ derivatives also are suitable in the form of capsules, tablets or coated tablets, which preferably contain 0.1 to 100 mg of active ingredient or are applied orally in the form of suspensions, which preferably contain 1-200 mg of active ingredient per dosage unit, and are also applied rectally to treat allergic diseases of the intestinal track, such as colitis ulcerosa and colitis granulomatosa.

The new leukotriene-B$_4$ derivatives can also be used combined with, e.g., lipoxygenase inhibitors, cyclooxygenase inhibitors, prostacyclin agonists, thromboxane antagonists, leukotriene-D$_4$ antagonists, leukotriene-E$_4$ antagonists, leukotriene-F$_4$ antagonists, phosphodiesterase inhibitors or PAF antagonists.

EXAMPLE 1

5-[2-[(1E,3E)-(5RS)-5-acetoxy-1,3-tridecadienyl]-phenyl]-pentan-1-ol

A solution of 3.97 ml of 1-bromooctane in 7 ml of ether is instilled in 559 mg of magnesium at 25° C. under argon and then stirred for 30 min. at 25° C.

2 ml of the Grignard solution obtained above is added to a solution of 301 mg of (2E,4E)-5-[2-(5-diphenyl-tert-butylsilyloxypentyl)-phenyl]-2,4-pentadienyl in 10 ml of ether, 2 ml of the Grignard solution obtained above is added at −20° C. under argon and stirred for 40 minutes at −20° C. The reaction mixture is poured on 50 ml of a saturated ammonium chloride solution, extracted three times with ether, the organic phase is shaken out with brine, dried on sodium sulfate and evaporated in a vacuum. The residue thus obtained is chromatographed on silica gel. With hexane/methyl-tert-butyl ether (9+1), 329 mg of 5-[2-[(1E,3E)-(5RS)-5-hydroxy-1,3-tridecadienyl]-phenyl]pentan-1-ol-diphenyl-tert-butylsilyl ether is obtained as a colorless oil.

IR (CHCl$_3$): 3603, 3440 (broad), 2930, 990 cm$^{-1}$.

For acetylation, 0.5 ml of acetic anhydride is added to a solution of 310 mg of the above-described alcohol in 2 ml of pyridine and stirred for 16 hours at 25° C. Then, it is concentrated by evaporation with adding toluene in a vacuum and the residue is chromatographed on silica gel. With hexane/1-5% of methyl-tert-butyl ether, 265 mg of 5-[(1E,3E)-(5RS)-5-acetoxy-1,3-tridecadienyl]-phenyl]-pentan-1-ol-diphenyl-tert-butylsilyl ether is obtained as a colorless oil.

IR (CHCl$_3$): 2932, 1728, 1245, 990 cm$^{-1}$.

For cleavage of silyl ether, 984 mg of tetrabutylammonium fluoride trihydrate is added to a solution of 200 mg of above-produced acetate in 4 ml of tetrahydrofuran and stirred for 1.5 hours at 24° C. Then, it is diluted with ether, washed with water, dried on sodium sulfate and concentrated by evaporation in a vacuum. The residue thus obtained is filtered on silica gel with hexane/ethyl acetate (1+1) and the solution is concentrated by evaporation in a vacuum. Then, the crude product is chromatographed on silica gel with hexane/10-50% of ethyl acetate. 92 mg of the title compound is obtained as a colorless oil.

IR (CHCl$_3$): 3625, 3480 (broad), 2930, 1728, 1248, 990 cm$^{-1}$.

The initial material for the above title compound is produced as follows:

a) 4-chlorobutan-1-ol-diphenyl-tert-butylsilyl ether 168 g of diphenyl-tert-butylsilyl chloride is added to a solution of 60 g of 4-chlorobutan-1-ol and 94 g of imidazole in 700 ml of dimethylformamide, at 0° C. under argon and then stirred for 16 hours at 24° C. Then, the reaction mixture is diluted with hexane/ether (8+2) and the organic phase is washed in succession once with water, twice with 10% sulfuric acid and once with semiconcentrated sodium chloride solution. After the drying on magnesium sulfate and filtration, it is concentrated by evaporation in a vacuum. The residue thus obtained is chromatographed on silica gel with hexane/methyl-tert-butyl ether (97+3). 181 g of the title compound is thus obtained as a colorless oil.

b) 2-(5-diphenyl-tert-butylsilyloxypentyl)-benzyl alcohol 200 ml of a 1.6 molar butyllithium solution in hexane is instilled in a solution of 16.3 g of 2-methylbenzyl alcohol, under argon at 0° C. After completion of the addition, it is refluxed for 5 hours. Then, it is cooled to 25° C. and 51.0 g of 4-chlorobutan-1-ol-diphenyl-tert-butylsilyl ether is instilled. After 16 hours of stirring at 25° C., it is diluted with ether and washed once with water. It is dried on magnesium sulfate and evaporated in a vacuum. The residue thus obtained is chromatographed on silica gel. With hexane/5-20% of ethyl acetate, 31.5 g of the title compound is obtained as a colorless oil.

IR (CHCl$_3$): 3610, 3450 (broad), 2935 cm$^{-1}$.

c) 2-(5-diphenyl-tert-butylsilyloxypentyl)-benzaldehyde 60.0 g of manganese dioxide is added to a solution of 21.4 g of 2-(5-diphenyl-tert-butylsilyloxypentyl)-benzyl alcohol in 600 ml of methylene chloride, and stirred for 4 hours at 25° C. Then, the reaction mixture is filtered on Celite, washed well with ethyl acetate and concentrated by evaporation in a vacuum. 19.9 g of the title compound is thus obtained as a colorless oil.

IR (CHCl$_3$): 2938, 2722, 1695, 1600 cm$^{-1}$.

d) (2E,4E)-5-[2-(5-diphenyl-tert-butylsilyloxypentyl)-phenyl]-2,4-pentadienoic acid ethyl ester A total of 5.9 g of potassium-tert-butylate is added in portions to a solution of 14 g of phosphonocrotonic acid triethyl ester in 130 ml of tetrahydrofuran at −20° C. under argon and is allowed to stir for 30 minutes at −20° C. Then, 14.3 g of 2-(5-diphenyl-tert-butylsilyloxypentyl)-benzaldehyde in 65 mol of tetrahydrofuran is instilled and stirred for 45 minutes at −20° C. Then, the reaction mixture is poured on water and extracted three times with methylene chloride. The organic phase is washed once with water, dried on sodium sulfate and concentrated by evaporation in a vacuum. The residue thus obtained is chromatographed with hexane/0–10% of methyl-tert-butyl ether on silica gel. 10.3 g of the title compound is obtained as a colorless oil.

IR (CHCl$_3$); 2938, 1702, 1625, 998 cm$^{-1}$.

e) (2E,4E)-5-[2-(5-diphenyl-tert-butylsilyloxypentyl)-phenyl]-2,4-pentadien-1-ol 22 ml of a 1.2 molar DIBAH solution in toluene is instilled in a solution of 4.0 g of (2E,4E)-5-[2-(5-diphenyl-tert-butylsilyloxypentyl)-phenyl]-2,4-pentadienoic acid ethyl ester in 100 ml of toluene at −70° C. under argon. After 1 hour of stirring at −70° C., 3 ml of isopropanol is carefully instilled in the reaction mixture followed by 11 ml of water and it is allowed to stir for 1 hour at 24° C. It is filtered, the precipitate is washed well with ethyl acetate and concentrated by evaporation in a vacuum. 3.6 g of the title compound is thus obtained as a colorless oil.

IR (CHCl$_3$): 3605, 3440 (broad), 2937, 990 cm$^{-1}$.

f) (2E,4E)-5-[2-(5-diphenyl-tert-butylsilyloxypentyl)-phenyl]-2,4-pentadienal 25 g of manganese dioxide is added to a solution of (2E,4E)-5-[2-(5-diphenyl-tert-butylsilyloxypentyl)-phenyl]-2,4-pentadien-1-ol in 100 ml of methylene chloride and stirred for 2 hours under argon at 25° C. Then, it is filtered on Celite, rewashed well with methylene chloride and concentrated by evaporation in a vacuum. 3.5 g of the title compound is thus obtained as a colorless oil.

IR (CHCl$_3$): 2938, 2745, 1680, 1620, 1602, 988 cm$^{-1}$.

EXAMPLE 2

5-[2-[(1E,3E)-(5RS)-5-acetoxy-1,3-undecadienyl]-phenyl]-pentan-1-ol

Analogously to example 1, 398 mg of 5-[2-[(1E,3E)-(5RS)-5-acetoxy-1,3-undecadienyl]-phenyl]-pentan-1-ol-diphenyl-tert-butylsilyl ether is obtained as a colorless oil from 486 mg of (2E,4E)-5-[2-(5-diphenyl-tert-butylsilyloxypentyl)-phenyl]-2,4-pentadienal (produced in example 1) by reaction with hexylmagnesium bromide solution.

IR (CHCl$_3$): 3595, 3440 (broad), 2910, 980 cm$^{-1}$.

By acetylation, 407 mg of 5-[2-[(1E,3E)-(5RS)-5-acetoxy-1,3-undecadienyl]-phenyl]-pentan-1-ol-diphenyl-tert-butylsilyl ether is obtained as a colorless oil from 396 mg of the above-described alcohol.

IR (CHCl$_3$): 2938, 1730, 1245, 990 cm$^{-1}$.

By silyl ether cleavage, starting from 407 mg of the above-produced acetate with 1.97 g of tetrabutylammonium fluoride trihydrate, 202 mg of the title compound is obtained as a colorless oil.

IR (CHCl$_3$): 3620, 3450 (broad), 2940, 1728, 1245, 990 cm$^{-1}$.

EXAMPLE 3

5-[2-[(1E,3E)-(5RS)-5-acetoxy-1,3-pentadecadienyl]-phenyl]-pentan-1-ol

Analogously to example 1, 592 mg of 5-[2-[(1E,3E)-(5RS)-5-hydroxy-1,3-pentadecadienyl]phenyl]-pentan-1-ol-diphenyl-tert-butylsilyl ether is obtained as a colorless oil from 497 mg of (2E,4E)-5-[2-(5-diphenyl-tert-butylsilyloxypentyl)-phenyl]-2,4-pentadienal (produced in example 1) by reaction with decylmagnesium bromide solution.

IR (CHCl$_3$): 3630, 3500 (broad), 2930, 990 cm$^{-1}$.

By acetylation, 592 mg of 5-[2-[(1E,3E)-(5RS)-5-acetoxy-1,3-pentadecadienyl]-phenyl]pentan-1-ol-diphenyl-tert-butylsilyl ether is obtained as a colorless oil from 592 mg of the above-described alcohol.

IR (CHCl$_3$): 2930, 1730, 1248, 990 cm$^{-1}$.

By silyl ether cleavage, starting from 580 mg of the above-produced acetate with 2.85 g of tetrabutylammonium fluoride trihydrate, 153 mg of the title compound is obtained as a colorless oil.

IR (CHCl$_3$): 3620, 3460 (broad), 2930, 1728, 1245, 990 cm$^{-1}$.

EXAMPLE 4

5-[2-[(3E)-(5RS)-5-acetoxy-1,3-tridecenyl]-phenyl]-pentan-1-ol

Analogously to example 1, 845 mg of 5-[2-[(3E)-(5RS)-5-hydroxy-3-tridecenyl]-phenyl]-pentan-1-ol-diphenyl-tert-butylsilyl ether is obtained as a colorless oil from 750 mg of (4E)-5-[2-(5-diphenyl-tert-butylsilyloxypentyl)-phenyl]-2-pentenal by reaction with octylmagnesium bromide solution.

IR (CHCl$_3$): 3622, 3480 (broad), 2930 cm$^{-1}$.

By acetylation, 867 mg of 5-[2-[(3E)-(5RS)-5-acetoxy-3-tridecenyl]-phenyl]-pentan-1-ol-diphenyl-tert-butylsilyl ether is obtained as a colorless oil from 842 mg of the above-described alcohol.

IR (CHCl$_3$): 2930, 1727, 1243 cm$^{-1}$.

By silyl ether cleavage, starting from 867 mg of the above-produced acetate with 4.26 g of tetrabutylammonium fluoride trihydrate, 287 mg of the title compound is obtained as a colorless oil.

IR (CHCl$_3$): 3620, 3460 (broad), 2938, 1725, 1250 cm$^{-1}$.

The initial material for the title compound in example 4 is produced as follows:

a) (2E)-3-[2-(5-diphenyl-tert-butylsilyloxypentyl)-phenyl]-2-propenoic acid ethyl ester 1.96 g of potassium-tert-butylate is added in portions to a solution of 4.78 g of phosphonoacetic acid triethyl ester in 100 ml of tetrahydrofuran at 0° C. under nitrogen. It is stirred for 10 minutes at 24° C. and then 5.0 g of 2-(5-diphenyl-tert-butylsilyloxypentyl)-benzaldehyde (produced in example 1) in 70 ml of toluene is instilled. After 5 hours of stirring at 24° C., it is diluted with 800 ml of ether and the organic phase is washed neutral with water. After the drying on sodium sulfate, it is concentrated by evaporation in a vacuum. The crude product thus obtained is chromatographed on silica gel. 5.8 of the title compound is obtained as a colorless oil with hexane/0–20% of ethyl acetate.

IR (CHCl$_3$): 2938, 1710, 1633, 1603, 980 cm$^{-1}$.

b)
(2E)-3-[2-(5-diphenyl-tert-butylsilyloxypentyl)-phenyl]-2-propen-1-ol 33 ml of a 1.2 molar DIBAH solution in toluene is instilled in a solution of 5.78 g of (2E)-3-[2-(5-diphenyl-tert-butylsilyloxypentyl)-phenyl]-2-propenoic acid ethyl ester in 170 ml of toluene at −70° C. under argon and stirred for 1 hour at −70° C. Then, 10 ml of isopropanol is carefully instilled, followed by 15 ml of water, and stirred for 1 hour at 24° C. After filtration, the precipitate is washed well with ethyl acetate and is concentrated by evaporation in a vacuum. The crude product thus obtained is chromatographed on silica gel. With hexane/0–25% of ethyl acetate, 4.94 g of the title compound is obtained as a colorless oil.

IR (CHCl$_3$): 3608, 3440 (broad), 2936, 970 cm$^{-1}$.

c)
3-[2-(5-diphenyl-tert-butylsilyloxypentyl)-phenyl]-propan-1-ol

A solution of 4.86 g of (2E)-3-[2-(5-diphenyl-tert-butylsilyloxypentyl)-phenyl]-2-propan-1-ol in 120 ml of ethyl acetate is mixed with 490 mg of 10% palladium-carbon and stirred in a hydrogen atmosphere for 5 hours at 25° C. After filtering of the catalyst, it is concentrated by evaporation in a vacuum. The crude product thus obtained is chromatographed on silica gel. With hexane/0–20% of ethyl acetate, 4.6 g of the title compound is obtained as a colorless oil.

IR (CHCl$_3$): 3620, 3450 (broad), 2938 cm$^{-1}$.

d)
3-[2-(5-diphenyl-tert-butylsilyloxypentyl)-phenyl]-propanal 35 g of Collins reagent is added in portions to a solution of 3.5 g of 3-[2-(5-diphenyl-tert-butylsilyloxypentyl)-phenyl]-propan-1-ol in 200 ml of methylene chloride at 0° C. under argon and stirred for 30 minutes at 24° C. Then, Celite is added to the reaction mixture. It is filtered on Celite, rewashed well with methylene chloride and concentrated by evaporation in a vacuum. The crude product thus obtained is chromatographed with hexane/ethyl acetate (9+1) on silica gel. 2.5 g of the title compound is obtained as a colorless oil.

IR (CHCl$_3$): 2938, 2742, 1728 cm$^{-1}$.

e)
(2E)-5-[2-(5-diphenyl-tert-butylsilyloxypentyl)-phenyl]-2-pentenoic acid ethyl ester 1.1 g of potassium-tert-butylate is added in portions to a solution of 2.7 g of phosphonoacetic acid triethyl ester in 50 ml of tetrahydrofuran at 0° C. under nitrogen. It is stirred for 10 minutes at 24° C. and then 2.5 g of 3-[2-(5-diphenyltert-butylsilyloxypentyl)-phenyl]-propanal in 40 ml of toluene is instilled. After 4 hours of stirring at 24° C., it is diluted with 400 ml of ether and the organic phase is washed neutral with water. After the drying on sodium sulfate, it is concentrated by evaporation in a vacuum. The crude product thus obtained is chromatographed on silica gel. 1.5 g of the title compound is obtained as a colorless oil with hexane/ethyl acetate (95+5).

IR (CHCl$_3$): 2939, 1714, 1655, 975 cm$^{-1}$.

f)
(2E)-5-[2-(5-diphenyl-tert-butylsilyloxypentyl)-phenyl]-2-penten-1-ol 5.5 ml of a 1.2 molar DIBAH solution in toluene is instilled in a solution of 1.0 g of (2E)-5-[2-(5-diphenyl-tert-butylsilyloxypentyl)-phenyl]-2-pentenoic acid ethyl ester in 33 ml of toluene at −70° C. under argon and stirred for 1 hour at −70° C. Then, 1 ml of isopropanol is carefully instilled, followed by 3 ml of water, and it is stirred for 1 hour at 25° C. After filtration, the precipitate is washed well with ethyl acetate and concentrated by evaporation in a vacuum. The crude product thus obtained is chromatographed on silica gel. With hexane/0–25% of ethyl acetate, 870 mg of the title compound is obtained as a colorless oil.

IR (CHCl$_3$): 3608, 3430 (broad), 2938, 972 cm$^{-1}$.

g)
(2E)-5-[2-(5-diphenyl-tert-butylsilyloxypentyl)-phenyl]-2-pentenal 6.0 g of manganese dioxide is added to a solution of 870 mg of (2E)-5-[2-(5-diphenyl-tert-butylsilyloxypentyl)-phenyl]-2-penten-1-ol in 30 ml of methylene chloride and stirred for 2 hours under argon at 25° C. Then, it is filtered on Celite, rewashed well with methylene chloride and concentrated by evaporation in a vacuum. The crude product thus obtained is chromatographed on silica gel with hexane/0–10% of ethyl acetate. 750 mg of the title compound is obtained as a colorless oil.

IR (CHCl$_3$): 2937, 2742, 1690, 1638, 875 cm$^{-1}$.

EXAMPLE 5

5-[2-(1E,3E)-(5RS)-5-acetoxy-1,3-tridecadienyl]-phenyl]-pentanoic acid 750 mg of Collins reagent is added to a solution of 92 mg of 5-[2-(1E,3E)-(5RS)-5-acetoxy-1,3-tridecadienyl]-phenyl]-pentan-1-ol (produced in example 1) in 10 ml of methylene chloride and is allowed to stir for 40 minutes at 0° C. under argon. Then, Celite is mixed and it is filtered on Celite, and it is rewashed well with a mixture of hexane/EE (1+1). After the concentration by evaporation in a vacuum, 92 mg of 5-[2-(1E,3E)-(5RS)-5-acetoxy-1,3-tridecadienyl]-phenyl]-pentanal is obtained, which is used without further purification in the next step.

IR (CHCl$_3$): 2930, 2735, 1727, 1245, 990 cm$^{-1}$.

0.2 ml of Jones reagent (J. Chem. Soc. 1953, 2555) is instilled in a solution of 92 mg of the above-produced aldehyde in 8 ml of acetone with stirring at −30° C. and is stirred for 15 minutes at −30° C. Then, 0.1 ml of isopropanol is added and stirred for 5 minutes at −20° C. Then, it is diluted with ether, washed neutral with saturated sodium chloride solution and dried on sodium sulfate. After the concentration by evaporation in a vacuum, the residue is chromatographed on silica gel. With hexane/30–50% of ethyl acetate, 53.8 mg of the title compound is obtained as a colorless oil.

IR (CHCl$_3$): 3520, 3350 (broad), 2930, 1724, 1245, 988 cm$^{-1}$.

EXAMPLE 6

5-[2-(1E,3E)-(5RS)-5-acetoxy-1,3-undecadienyl]-phenyl]-pentanoic acid

Analogously to example 5, 179 mg of 5-[2-(1E,3E)-(5RS)-5-acetoxy-1,3-tridecadienyl]-phenyl]-pentanal is obtained from 180 mg of 5-[2-(1E,3E)-(5RS)-5-acetoxy- 1,3-tridecadienyl]-phenyl]-pentan-1-ol (produced in example 2).

IR (CHCl$_3$): 2938, 2730, 1725, 1245, 990 cm$^{-1}$.

Starting from the 179 mg of the above-produced aldehyde, 71 mg of the title compound is obtained, analogously to example 5, as a colorless oil.

IR (CHCl$_3$): 3520, 3350 (broad), 2938, 1728, 1245, 988 cm$^{-1}$.

EXAMPLE 7

5-[2-(1E,3E)-(5RS)-5-acetoxy-1,3-pentadecadienyl]-phenyl]-pentanoic acid

Analogously to example 5, 139 mg of 5-[2-(1E,3E)-(5RS)-5-acetoxy-1,3-pentadecadienyl]-phenyl]-pentanal is obtained from 140 mg of 5-[2-(1E,3E)-(5RS)-5-acetoxy-1,3-pentadecadienyl]-phenyl]-pentan-1-ol (produced in example 3).

IR (CHCl$_3$): 2938, 2732, 1725, 1245, 990 cm$^{-1}$.

Starting from 139 mg of the above-produced aldehyde, 75 mg of the title compound is obtained, analogously to example 5, as a colorless oil.

IR (CHCl$_3$): 3520, 3350 (broad), 2930, 1723, 1245, 988 cm$^{-1}$.

EXAMPLE 8

5-[2-[(3E)-(5RS)-5-acetoxy-3-tridecenyl]-phenyl]-pentanoic acid

Analogously to example 5, 148 mg of 5-[2-[(3E)-(5RS)-5-acetoxy-3-tridecenyl]-phenyl]-pentanal is obtained from 150 mg of 5-[2-[(3E)-(5RS)-5-acetoxy-3-tridecenyl]-phenyl]-pentan-1-ol (produced in example 4).

IR (CHCl$_3$); 2930, 2728, 1723, 1250, 970 cm$^{-1}$.

Starting from the 148 mg of the above-produced aldehyde, 55 mg of the title compound is obtained, analogously to example 5, as a colorless oil.

IR (CHCl$_3$): 3520, 3350 (broad), 2932, 1736, 1709, 1240, 970 cm$^{-1}$.

EXAMPLE 9

5-[2-[(1E,3E)-(5RS)-5-hydroxy-1,3-tridecadienyl]-phenyl]-pentanoic acid 0.3 ml of a 0.5 normal sodium hydroxide solution is added to a solution of 12 mg of 5-[2-[(1E,3E)-(5RS)-5-acetoxy-1,3-tridecadienyl]-phenyl]-pentanoic acid (produced in example 5) in 0.3 ml of methanol at 25° C. and stirred for 4 hours at 24° C. Then, it is cooled to 0° C. and acidified with a 0.5 normal sulfuric acid to pH=6. It is extracted four times with ethyl acetate, the organic phase is washed with water and dried on sodium sulfate. It is concentrated by evaporation in a vacuum, and the residue is chromatographed on silica gel. With ether/hexane (7+3) as a mobile solvent, 3.8 g of the title compound is obtained as a colorless oil.

IR (CHCl$_3$): 3600, 3520, 3400 (broad), 2928, 1710, 988 cm$^{-1}$.

EXAMPLE 10

5-[2-[(1E,3E)-(5RS)-5-hydroxy-1,3-undecadienyl]-phenyl]-pentanoic acid

Analogously to example 9, 28 mg of the title compound is obtained as a colorless oil from 60 mg of 5-[2-[(1E,3E)-(5RS)-5-acetoxy-1,3-undecadienyl]-phenyl]-pentanoic acid (produced in example 6).

IR (KBr): 3410 (broad), 2930, 1708, 988 cm$^{-1}$.

EXAMPLE 11

5-[2-[(1E,3E)-(5RS)-5-hydroxy-1,3-pentadecadienyl]-phenyl]-pentanoic acid

Analogously to example 9, 15 mg of the title compound is obtained as a colorless oil from 62 mg of 5-[2-[(1E,3E)-(5RS)-5-acetoxy-1,3-pentadecadienyl]-phenyl]-pentanoic acid (produced in example 7).

IR (CHCl$_3$): 3600, 3520, 3400 (broad), 2930, 1713, 990 cm$^{-1}$.

EXAMPLE 12

5-[2-[(3E)-(5RS)-5-hydroxy-3-tridecenyl]-phenyl]-pentanoic acid

Analogously to example 9, 32 mg of the title compound is obtained as a colorless oil from 45 mg of 5-[2-[(3E)-(5RS)-5-acetoxy-3-tridecenyl]-phenyl]-pentanoic acid (produced in example 8).

IR (CHCl$_3$): 3605, 3520, 3400 (broad), 2932, 1712, 972 cm$^{-1}$.

EXAMPLE 13

5-[2-[(1E,3E)-(5RS)-5-hydroxy-1,3-tridecadienyl]-phenyl]-pentan-1-ol 6.7 ml of a 0.5 normal sodium hydroxide solution is added to a solution of 270 mg of 5-[2-[(1E,3E)-(5RS)-5-acetoxy-1,3-tridecadienyl]-phenyl]-pentan-1-ol (produced in example 1) in 11.7 ml of methanol and the reaction mixture is stirred for 16 hours at 25° C. Then, it is cooled to 0° C. and acidified with a 0.5 normal sulfuric acid to pH=6. It is extracted three times with methylene chloride and the organic phase is dried on sodium sulfate. It is concentrated by evaporation in a vacuum, and the residue is chromatographed on silica gel. With hexane/50–80% of ethyl acetate as a mobile solvent, 184 mg of the title compound is obtained as a colorless oil.

IR (CHCl$_3$): 3350 (broad), 2930, 988 cm$^{-1}$.

EXAMPLE 14

5-[2-[(1E,3E)-(5RS)-5-hydroxy-1,3-tridecadienyl]-phenyl]-pentanoic acid methyl ester An ethereal diazomethane solution is added to a solution of 5 mg of 5-[2-[(1E,3E)-(5RS)-5-hydroxy-1,3-tridecadienyl]-phenyl]-pentanoic acid (produced in example 9) in 0.5 ml of methylene chloride at 0° C. until permanent yellow dyeing and stirred for 5 minutes at 0° C. Then, it is concentrated by evaporation in a vacuum and the residue is chromatographed on silica gel. With hexane/0–80% of ether, 2.6 mg of the title compound is obtained as a colorless oil.

IR (CHCl$_3$): 3620, 3480 (broad), 2930, 1730, 988 cm$^{-1}$.

EXAMPLE 15

5-[2-[(1E,3E)-(5RS)-5-hydroxy-1,3-tridecadienyl]-phenyl]-pentanoic acid ethyl ester Analogously to example 14, 1.8 mg of the title compound is obtained as a colorless oil from 3.7 mg of the acid, produced in example 9, with diazoethane.

IR (CHCl$_3$): 3620, 3480 (broad), 2930, 1732, 990 cm$^{-1}$.

EXAMPLE 16

5-[2-[(1E,3E)-(5RS)-5-hydroxy-1,3-tridecadienyl]-phenyl]-pentanoic acid-tris(hydroxymethyl)-aminomethane salt A solution of 5 mg of tris-(hydroxymethyl)-aminomethane in 0.02 ml of water is added to a solution of 13 mg of the acid, produced according to example 9, in 2 ml of acetonitrile at 70° C. It is allowed to cool with stirring, decanted after 16 hours from the solvent and the residue is dried in a vacuum. 9 mg of the title compound is isolated as a waxy mass.

EXAMPLE 17

5-[2-[(5RS)-5-hydroxy-tridecanyl]-phenyl]-pentanoic acid

A solution of 60 mg of the acid, produced according to example 9, in 4 ml of ethyl acetate is mixed with 12 mg of palladium 10% on carbon, and the suspension is stirred for 3 hours at 24° C. in a hydrogen atmosphere. Then, it is filtered from the catalyst and concentrated by evaporation in a vacuum. The residue thus obtained is chromatographed on silica gel. With ether/hexane (7+3) as a mobile solvent, 38 mg of the title compound is obtained as a colorless oil.

IR (CHCl$_3$); 3600, 3440 (broad), 2925, 1710 cm$^{-1}$.

EXAMPLE 18

5-[2-[(5RS)-5-acetoxy-tridecanyl]-phenyl]-pentanoic acid

Analogously to example 17, 29 mg of the title compound is obtained as a colorless oil from 46 mg of the acid produced in example 5.

IR (CHCl$_3$): 3600, 3520, 3350, 2930, 1722, 1712, 1255 cm$^{-1}$.

We claim:

1. Leukotriene-B$_4$ analogs of formula I,

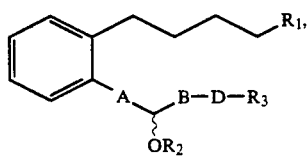

(I)

in which

R$_1$ is COOR$_4$ with R$_4$ meaning a hydrogen atom, an alkyl radical with 1-10 C atoms, a cycloalkyl radical with 3-10 C atoms, an aryl radical with 6-10 C atoms optionally substituted by 1-2 chlorine, bromine, phenyl, alkyl with 1-4 C atoms, chloromethyl, fluoromethyl or trifluoromethyl, A means a trans, trans—CH=CH—CH=CH— group, trans—CH$_2$—CH$_2$—CH=CH group or a tetramethylene group, B means a straight-chain or branched-chain, saturated or unsaturated alkylene group with up to 10 C atoms which can optionally be substituted by fluorine, D means a direct bond, a —C≡C— group or a —CH=CR$_6$ group with R6 as hydrogen, C$_1$-C$_5$ alkyl, chlorine or bromine, or B and D together mean a direct bond, R$_2$ means a hydrogen atom or an acid radical of an organic acid with 1-15 C atoms and R$_3$ means a hydrogen atom, an alkyl radical with 1-10 C atoms, or an alkyl radical with 1-10 C atoms substituted by chlorine or bromine and, if R$_4$ means a hydrogen atom, their salts with physiologically compatible bases and their cyclodextrin clathrates.

2. 5-[2-[(1E,3E)-(5RS)-5-acetoxy-1,3-tridecadienyl]-phenyl]-pentanoic acid a compound of claim 1.

3. 5-[2-[(1E,3E)-(5RS)-5-acetoxy-1,3-undecadienyl]-phenyl]-pentanoic acid a compound of claim 1.

4. 5-[2-[(1E,3E)-(5RS)-5-acetoxy-1,3-pentadecadienyl]-phenyl]-pentanoic acid a compound of claim 1.

5. 5-[2-[(3E)-(5RS)-5-acetoxy-3-tridecenyl]-phenyl]-pentanoic acid a compound of claim 1.

6. 5-[2-[(1E,3E)-(5RS)-5-hydroxy-1,3-tridecadienyl]-phenyl]-pentanoic acid a compound of claim 1.

7. 5-[2-[(1E,3E)-(5RS)-5-hydroxy-1,3-undecadienyl]-phenyl]-pentanoic acid a compound of claim 1.

8. 5-[2-[(1E,3E)-(5RS)-5-hydroxy-1,3-pentadecadienyl]-phenyl]-pentanoic acid a compound of claim 1.

9. 5-[2-[(3E)-(5RS)-5-hydroxy-3-tridecenyl]-phenyl]-pentanoic acid a compound of claim 1.

10. 5-[2-[(1E,3E)-(5RS)-5-hydroxy-1,3-tridecadienyl]-phenyl]-pentanoic acid methyl ester a compound of claim 1.

11. 5-[2-[(1E,3E)-(5RS)-5-hydroxy-1,3-tridecadienyl]-phenyl]-pentanoic acid ethyl ester a compound of claim 1.

12. 5-[2-[(1E,3E)-(5RS)-5-hydroxy-1,3-tridecadienyl]-phenyl]-pentanoic acid-tris(hydroxymethyl)-aminomethane salt a compound of claim 1.

13. 5-[2-[(5RS)-5-hydroxy-tridecanyl]-phenyl]-pentanoic acid a compound of claim 1.

14. 5-[2-[(5RS)-5-acetoxy-tridecanyl]-phenyl]-pentanoic acid a compound of claim 1.

15. A pharmaceutical composition comprising one or more compounds according to claim 1 and an auxiliary agent or vehicle.

* * * * *